(12) United States Patent
Iida et al.

(10) Patent No.: US 10,458,954 B2
(45) Date of Patent: Oct. 29, 2019

(54) STRUCTURE EVALUATION SYSTEM, STRUCTURE EVALUATION APPARATUS, AND STRUCTURE EVALUATION METHOD

(71) Applicant: Kabushiki Kaisha Toshiba, Tokyo (JP)

(72) Inventors: Sanae Iida, Kanagawa (JP); Takashi Usui, Saitama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 195 days.

(21) Appl. No.: 15/454,182

(22) Filed: Mar. 9, 2017

(65) Prior Publication Data
US 2018/0074023 A1 Mar. 15, 2018

Related U.S. Application Data

(63) Continuation of application No. PCT/JP2017/007982, filed on Feb. 28, 2017.

(30) Foreign Application Priority Data

Sep. 15, 2016 (JP) ................ 2016-180914

(51) Int. Cl.
*G01N 29/14* (2006.01)
*G01N 29/44* (2006.01)
(Continued)

(52) U.S. Cl.
CPC .......... *G01N 29/14* (2013.01); *G01M 5/0008* (2013.01); *G01N 29/0672* (2013.01);
(Continued)

(58) Field of Classification Search
CPC .... G01N 29/14; G01N 29/0672; G01N 29/07; G01N 29/4445; G01N 2291/011; G01N 2291/0258; G01M 5/0008
(Continued)

(56) References Cited

U.S. PATENT DOCUMENTS 4,531,411 A 7/1985 Collins et al.
5,457,994 A 10/1995 Kwun et al.
(Continued)

FOREIGN PATENT DOCUMENTS

JP 59-87357 5/1984
JP 2006-10595 1/2006
(Continued)

OTHER PUBLICATIONS

Kawai, "Study on Damage evaluation of civil engineering structures by AE tomography method," Kyoto University (2011), pp. cover page, i-iii, and 1-91.
(Continued)

*Primary Examiner* — Nimeshkumar D Patel
*Assistant Examiner* — Tarun Sinha
(74) *Attorney, Agent, or Firm* — Finnegan, Henderson, Farabow, Garrett & Dunner, L.L.P.

(57) ABSTRACT

According to an embodiment, a structure evaluation system has a plurality of sensors, a signal processor, and an evaluator. The sensors detect an elastic wave generated from a structure. The signal processor acquires a reliability from a source of the elastic wave to the plurality of sensors by performing signal processing on the elastic wave detected by the plurality of sensors. The evaluator evaluates the soundness of the structure on the basis of the acquired reliability.

17 Claims, 12 Drawing Sheets

(51) Int. Cl.
*G01M 5/00* (2006.01)
*G01N 29/06* (2006.01)
*G01N 29/07* (2006.01)

(52) U.S. Cl.
CPC ......... *G01N 29/07* (2013.01); *G01N 29/4445* (2013.01); *G01N 2291/011* (2013.01); *G01N 2291/0258* (2013.01)

(58) Field of Classification Search
USPC .......................................................... 73/587
See application file for complete search history.

(56) References Cited

U.S. PATENT DOCUMENTS

| | | | |
|---|---|---|---|
| 6,122,312 | A | 9/2000 | Shiro |
| 7,912,481 | B2 | 3/2011 | Fujiwara et al. |
| 2007/0175279 | A1* | 8/2007 | Beard .................... G01N 29/32 73/584 |
| 2008/0019433 | A1 | 1/2008 | Yamanouchi et al. |
| 2009/0070048 | A1* | 3/2009 | Stothers .............. G01N 29/045 702/39 |
| 2010/0050778 | A1* | 3/2010 | Herley ................... G01L 5/246 73/761 |
| 2010/0319452 | A1 | 12/2010 | Masuda |
| 2013/0074600 | A1 | 3/2013 | Hunter et al. |
| 2013/0191040 | A1 | 7/2013 | Yoon et al. |
| 2014/0309950 | A1* | 10/2014 | Janapati .................... G01L 1/16 702/35 |
| 2015/0338380 | A1 | 11/2015 | Ziehl et al. |
| 2016/0084938 | A1 | 3/2016 | Doi et al. |
| 2016/0139084 | A1 | 5/2016 | Usui et al. |
| 2016/0262310 | A1 | 9/2016 | Usui et al. |
| 2016/0310044 | A1 | 10/2016 | Maeno et al. |
| 2016/0338603 | A1 | 11/2016 | Nakata et al. |
| 2017/0074833 | A1 | 3/2017 | Takamine |

FOREIGN PATENT DOCUMENTS

| | | |
|---|---|---|
| JP | 2007-198907 | 8/2007 |
| JP | 2014-95555 | 5/2014 |
| JP | 2014-174040 | 9/2014 |
| JP | 2016-61740 | 4/2016 |
| JP | 2016-99119 | 5/2016 |

OTHER PUBLICATIONS

Momoki, "Study on elastic wave tomography method for soundness evaluation of concrete structure," Kyoto University (2014), pp. cover page, index pages, and 1-141.

* cited by examiner

STRUCTURE EVALUATION SYSTEM, STRUCTURE EVALUATION APPARATUS, AND STRUCTURE EVALUATION METHOD

TECHNICAL FIELD

The present invention relates to a structure evaluation system, a structure evaluation apparatus, and a structure evaluation method.

BACKGROUND ART

In recent years, problems related to aging of structures such as bridges constructed during the period of high economic growth have become noticeable. Because loss is immeasurable when an accident occurs in a structure, technologies for monitoring a state of a structure have been proposed. For example, a technology for detecting damage to a structure by an acoustic emission (AE) method in which an elastic wave generated due to occurrence of an internal crack or progress of an internal crack is detected by a high-sensitivity sensor has been proposed. AE is an elastic wave generated due to a progress of fatigue crack of a material. In the AE method, an elastic wave is detected as an AE signal (voltage signal) by an AE sensor using a piezoelectric element. The AE signal is detected as an indication before breakage of the material occurs. Therefore, the frequency of occurrence of AE signals and the signal intensity are useful as an index indicating the soundness of the material. For this reason, studies are being carried out on technologies for detecting signs of deterioration of structures by the AE method.

A tomographic method is known as one of methods for evaluating a structure using an AE signal. Tomography is one of inverse analysis methods for estimating a velocity field structure inside a measurement region by using an arrival time difference between acoustic signals detected by a plurality of sensors, and can be used as a nondestructive inspection method for detecting a damaged part as a change in velocity field. Particularly, a method using an AE signal generated from inside a material as a signal source is known as AE tomography. However, in the conventional method, it is necessary to calculate component parameters iteratively by a simultaneous iterative method until a residual difference between a measured travel time and a theoretical travel time converges to within a tolerance range. For this reason, a considerable amount of calculation time is required for evaluating a structure in some cases.

CITATION LIST

Patent Literature

[Patent Literature 1]
Japanese Unexamined Patent Application, First Publication No. 2014-95555

SUMMARY OF INVENTION

Technical Problem

An objective of the present invention is to provide a structure evaluation system, a structure evaluation apparatus, and a structure evaluation method capable of reducing an amount of time required for evaluation of a structure.

Solution to Problem

According to an embodiment, a structure evaluation system has a plurality of sensors, a signal processor, and an evaluator. The sensors detect an elastic wave generated from a structure. The signal processor acquires a reliability from a source of the elastic wave to the plurality of sensors by performing signal processing on the elastic wave detected by the plurality of sensors. The evaluator evaluates the soundness of the structure on the basis of the acquired reliability.

DESCRIPTION OF EMBODIMENTS

Hereinafter, a structure evaluation system, a structure evaluation apparatus, and a structure evaluation method according to an embodiment will be described with reference to the drawings.

(First Embodiment)

Figure 1:
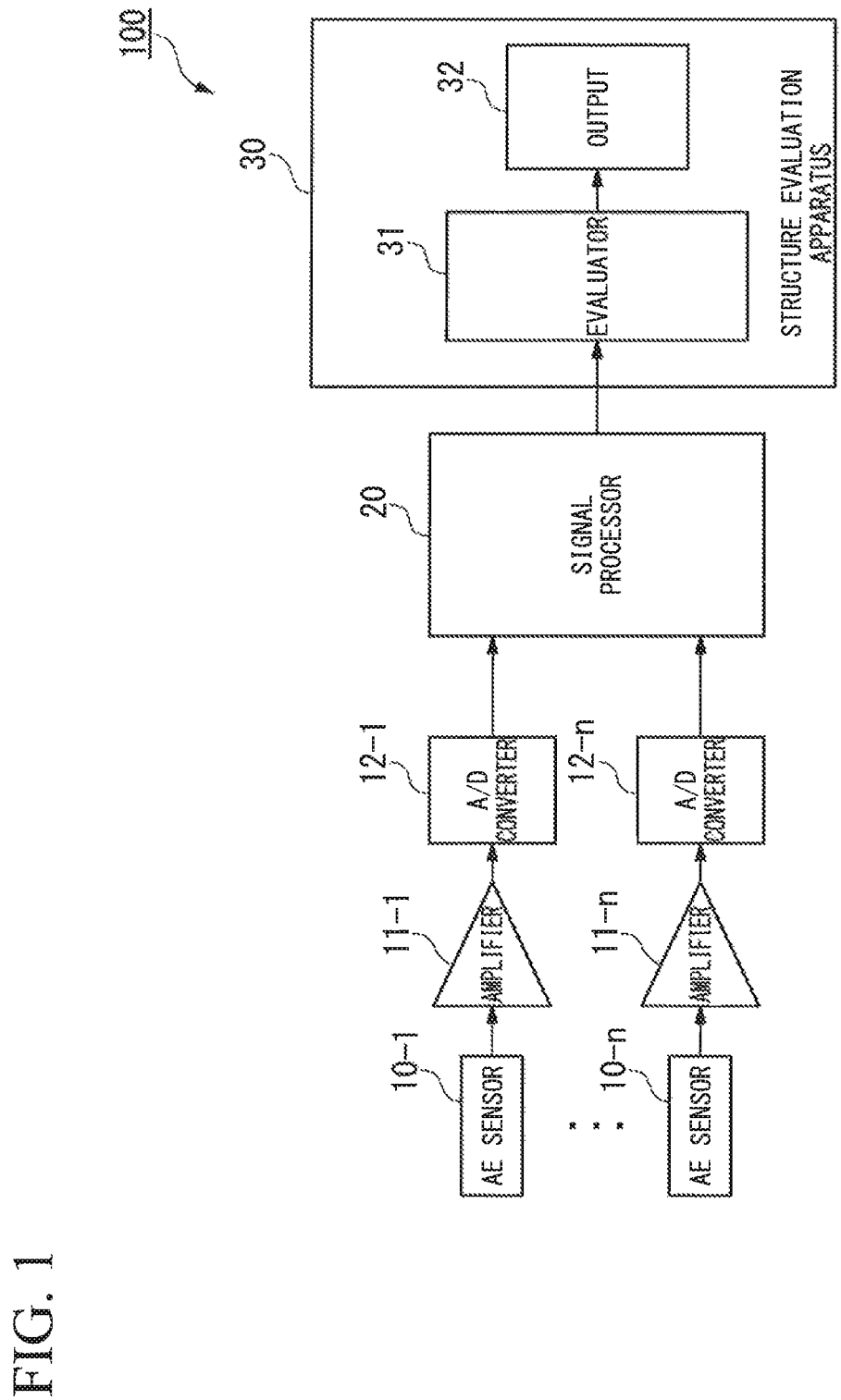
FIG. 1 is a view illustrating a system configuration of a structure evaluation system 100 according to a first embodiment.

FIG. 1 is a view illustrating a system configuration of the structure evaluation system 100 according to a first embodiment. The structure evaluation system 100 is used to evaluate the soundness of a structure. In the embodiments, the term evaluation refers to determining a degree of soundness of a structure, or a state of deterioration of the structure, based on a standard or standards. Also, although a bridge is described as an example of a structure in the embodiment, a structure is not necessarily limited to a bridge. For example, a structure may be any structure as long as an elastic wave is generated in the structure due to occurrence or progress of cracks or an external impact (e.g., rain, artificial rain, etc.). Also, a bridge is not limited to a structure constructed over a river or a valley, and includes various structures provided above the ground (e.g., an elevated bridge over a highway).

The structure evaluation system 100 includes a plurality of acoustic emission (AE) sensors 10-1 to 10-$n$ ($n$ is an integer equal to or greater than 2), a plurality of amplifiers 11-1 to 11-$n$, a plurality of analog-to-digital (A/D) converters 12-1 to 12-$n$, a signal processor 20, and a structure evaluation apparatus 30. The signal processor 20 and the structure evaluation apparatus 30 are connected to be able to communicate via a wire. Further, in the description below, the AE sensors 10-1 to 10-$n$ are referred to as an AE sensor 10 when not distinguished, the amplifiers 11-1 to 11-$n$ are referred to as an amplifier 11 when not distinguished, and the A/D converters 12-1 to 12-$n$ are referred to as an A/D converter 12 when not distinguished.

The AE sensor 10 is installed in a structure. For example, the AE sensor 10 is installed on a concrete floor slab of a bridge. The AE sensor 10 detects an elastic wave (an AE wave) generated from the structure and converts the detected elastic wave into a voltage signal. For the AE sensor 10, for example, a piezoelectric element having sensitivity in the range of 10 kHz to 1 MHz is used. Although the AE sensor 10 includes a resonance type having a resonance peak within a frequency range, a wide band type in which resonance is suppressed, and the like, any type of the AE sensor 10 may be used. Also, although a method of detecting an elastic wave by the AE sensor 10 includes a voltage output type, a resistance change type, a capacitance type and the like, any detection method may be used. The AE sensor 10 outputs a voltage signal to the amplifier 11. Instead of the AE sensor 10, an acceleration sensor can be used. In this case, the acceleration sensor performs processing similar to the processing by the AE sensor 10 to generate a processed signal and output the processed signal to the signal processor 11. The thickness of a concrete slab is at least 15 cm.

The amplifier 11 amplifies the voltage signal output from the AE sensor 10 and outputs the amplified voltage signal to the A/D converter 12.

Upon receiving the amplified signal, the A/D converter 12 quantizes the signal and converts the signal into a digital signal. The A/D converter 12 outputs the signal to the signal processor 20 as digital time-series data.

The signal processor 20 receives the time-series digital signal output from the A/D converter 12 as an input. The signal processor 20 performs signal processing on the input digital signal to obtain a reliability, which is an index of deterioration evaluation on an arrival path of an elastic wave from a source of the elastic wave to the AE sensor 10, for each elastic wave. The signal processor 20 outputs transmission data including the acquired reliability for each elastic wave to the structure evaluation apparatus 30.

The structure evaluation apparatus 30 includes a central processing unit (CPU), a memory, an auxiliary storage device or the like connected via a bus, and executes an evaluation program. By executing the evaluation program, the structure evaluation apparatus 30 functions as an apparatus including the evaluator 31 and an output 32. Further, all or some of the functions of the structure evaluation apparatus 30 may be realized by using hardware such as an application specific integrated circuit (ASIC), a programmable logic device (PLD), a field programmable gate array (FPGA), or the like. Also, the evaluation program may be recorded in a computer-readable recording medium. The computer-readable recording medium is, for example, a portable medium such as a flexible disk, a magneto-optical disk, a read-only memory (ROM), a compact disc (CD)-ROM or the like, or a storage device such as a hard disk embedded in a computer system. Also, the evaluation program may be transmitted and received via an electric communication line.

The evaluator 31 receives the transmission data output from the signal processor 20 as an input. The evaluator 31 evaluates the soundness of the structure on the basis of the reliability included in the input transmission data.

The output 32 is an image display device such as a liquid crystal display or an organic electro-luminescence (EL) display. The output 32 displays an evaluation result in accordance with the control of the evaluator 31. The output 32 may be an interface for connecting the image display device to the structure evaluation apparatus 30. In this case, the output 32 generates an image signal for displaying the evaluation result and outputs the image signal to the image display device connected thereto.

Figure 2:
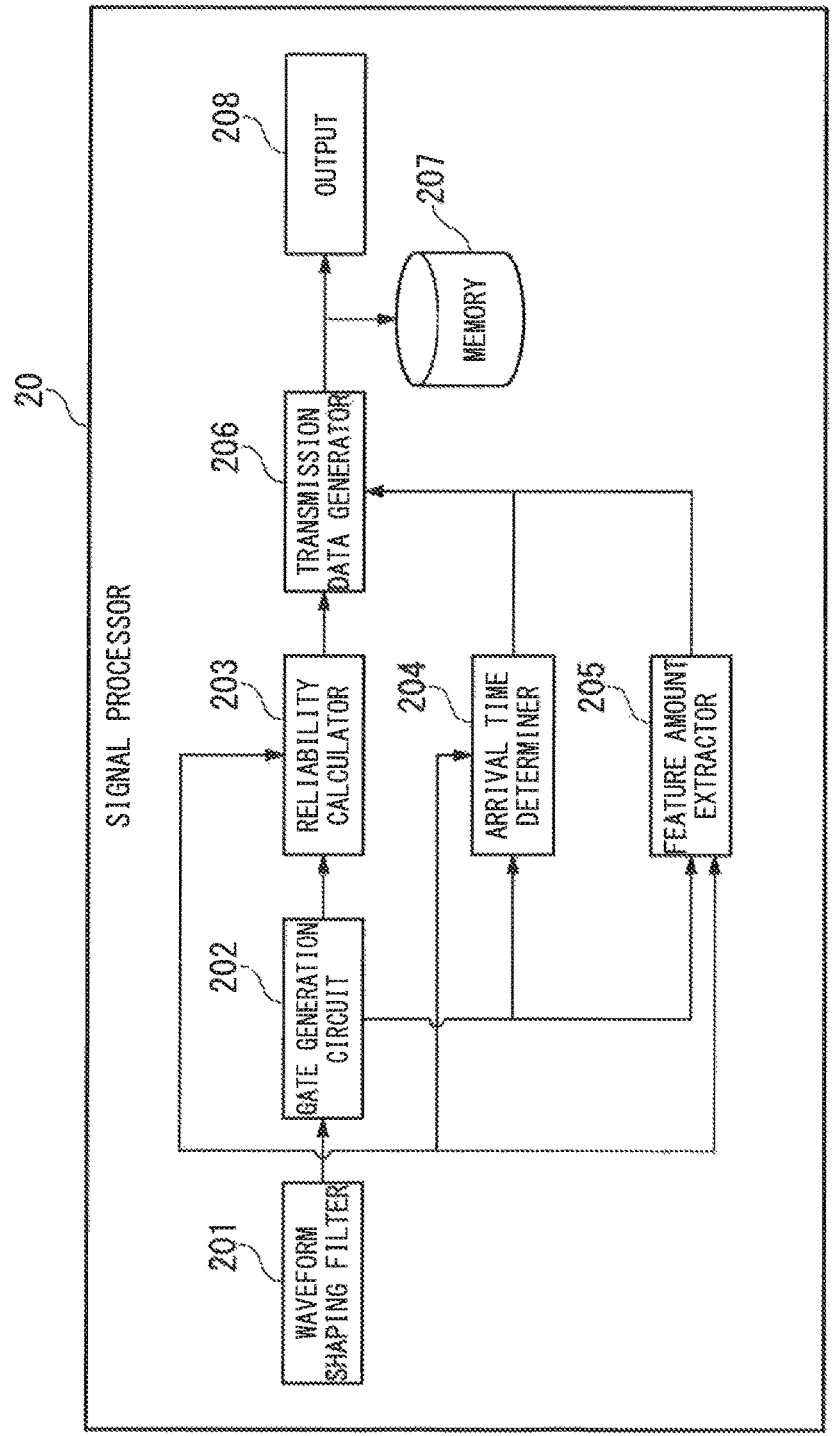
FIG. 2 is a schematic block diagram illustrating a function of a signal processor 20.

FIG. 2 is a schematic block diagram illustrating a function of the signal processor 20. As illustrated in FIG. 2, the signal processor 20 includes a waveform shaping filter 201, a gate generation circuit 202, a reliability calculator 203, an arrival time determiner 204, a feature amount extractor 205, a transmission data generator 206, a memory 207, and an output 208.

The waveform shaping filter 201 is, for example, a digital band-pass filter (BPF), and removes a noise component outside a predetermined signal band from the input time-series data. The waveform shaping filter 201 outputs a signal from which a noise component is removed (hereinafter referred to as "noise-removed AE signal") to the gate generation circuit 202, the reliability calculator 203, the arrival time determiner 204, and the feature amount extractor 205.

The gate generation circuit 202 receives the noise-removed AE signal output from the waveform shaping filter 201 as an input. The gate generation circuit 202 generates a gate signal that indicates whether the waveform of the input noise-removed AE signal is continued. The gate generation circuit 202 is realized by, for example, an envelope detector and a comparator. The envelope detector detects an envelope of the noise-removed AE signal. The comparator determines whether the envelope of the noise-removed AE signal is a predetermined threshold value or larger. From this, when the envelope of the noise-removed AE signal is the predetermined threshold value or larger, the gate generation circuit 202 outputs a gate signal (High) indicating that the waveform of the noise-removed AE signal is continued to the reliability calculator 203, the arrival time determiner 204, and the feature amount extractor 205. When the envelope of the noise-removed AE signal is less than the predetermined threshold value, the gate generation circuit 202 outputs a gate signal (Low) indicating that the waveform of the noise-removed AE signal is not continued to the reliability calculator 203, the arrival time determiner 204, and the feature amount extractor 205.

The reliability calculator 203 receives the noise-removed AE signal output from the waveform shaping filter 201 and a gate signal output from the gate generation circuit 202 as inputs. Based on the input gate signal, the reliability calculator 203 calculates the reliability of the noise-removed AE signal while the waveform of the noise-removed AE signal is continued.

The reliability can be expressed by a value and can refer to the degree of unexpectedness of the latest data with respect to data. Examples of the data may be past statistical data, data obtained at a past timing, data created by a user in a way such as hand-writing. The embodiment will be described in such a case that the reliability can be expressed by a value and can refer to the degree of unexpectedness of the latest data with respect to past statistical data. By referring to the past statistical data, the probability distribution related to the magnitude of a signal in a normal state can be obtained. The probability that the latest data will be generated can be obtained by applying the latest data to the probability distribution obtained from the past data. The probability that data similar to the past data will be generated is high, and the probability that data having properties different from those of the past data will be generated is low. That is, when the probability is higher (the reciprocal of the probability is smaller), an AE signal can be regarded as having a lower reliability, and, when the probability is lower (the reciprocal of the probability is larger), an AE signal can be regarded as having a higher reliability.

On the other hand, an elastic wave, which is an unexpected event caused by the occurrence or progress of cracks, is generated from a source having significantly different properties from those of a source in a normal state (state of high reliability). Then, by propagating inside the structure, the elastic wave is influenced by the inside of the structure, repeats being attenuated, diffused and reflected, and gradually loses its features (state of low reliability). When an AE signal close to a situation of a source is assumed as being in the state of high reliability and an AE signal close to noise is assumed as being in the state of low reliability, the reliability of an AE signal detected by the sensor may be considered as a result reflecting an inner structure of a propagation path. In the embodiment, the reliability calculator 203 uses a Shannon's information quantity related to the time-series data sampled from the noise-removed AE signal, a value obtained by smoothing the Shannon's information quantity, and a value obtained by calculating a Shannon's information quantity again related to the above value obtained by smoothing the Shannon's information quantity and smoothing the re-calculated Shannon's information quantity, as reliability values. The reliability calculator 203 outputs the calculated reliability information to the transmission data generator 206.

The arrival time determiner 204 receives the noise-removed AE signal output from the waveform shaping filter 201 and the gate signal output from the gate generation circuit 202 as inputs. The arrival time determiner 204 determines a time when the noise-removed AE signal exceeds a predetermined threshold value, a time when the reliability of the data has the maximum value, or a time when a predetermined standard, in which the threshold value and the reliability information are combined, is satisfied as the arrival time. The arrival time represents a reception time of an elastic wave. The arrival time determiner 204 outputs the determined time information to the transmission data generator 206.

On the basis of the gate signal, the feature amount extractor 205 extracts a feature amount of the noise-removed AE signal when the waveform of the noise-removed AE signal is continued. The feature amount is information indicating a feature of the noise-removed AE signal. For example, the feature amount may be an amplitude [mV] of the waveform of the noise-removed AE signal, a rise time [psec] of the gate signal, a duration time [μsec] of the gate signal, a zero-crossing count number [times] of the noise-removed AE signal, an energy of the waveform of the noise-removed AE signal [arb.], a frequency [Hz] of the noise-removed AE signal, etc. The feature amount extractor 205 outputs the extracted parameter related to the feature amount to the transmission data generator 206. When outputting the parameter related to the feature amount, the feature amount extractor 205 associates a sensor ID with the parameter related to the feature amount. The sensor ID represents identification information for identifying the AE sensor 10 installed in a region to be evaluated for the soundness of the structure (hereinafter referred to as "evaluation region.").

Here, the amplitude of the noise-removed AE signal is, for example, the maximum amplitude value of the noise-removed AE signal. The rise time of the gate signal is, for example, a time T1 until the gate signal rises above a preset predetermined value from zero. The duration time of the gate signal is, for example, an amount of time from the start of the rise of the gate signal until the amplitude becomes smaller than a preset value. The zero-crossing count number of the noise-removed AE signal is, for example, the number of times that the noise-removed AE signal crosses a reference line passing through a zero value. The energy of the waveform of the noise-removed AE signal is, for example, a value obtained by time integration of the square of the amplitude at each time point. Also, the definition of energy is not limited to the above example, and may be, for example, one approximated by using an envelope of a waveform. The frequency of the noise-removed AE signal is the frequency of the noise-removed AE signal.

The transmission data generator 206 receives the reliability information output from the reliability calculator 203, the time information indicating the reception time output from the arrival time determiner 204, and the parameter related to the feature amount output from the feature amount extractor 205 as inputs. The transmission data generator 206 generates transmission data by associating the input information.

The memory 207 is, for example, a dual port random access memory (RAM). The memory 207 stores transmission data.

The output 208 sequentially outputs the transmission data stored in the memory 207 to the structure evaluation apparatus 30.

Figure 3:
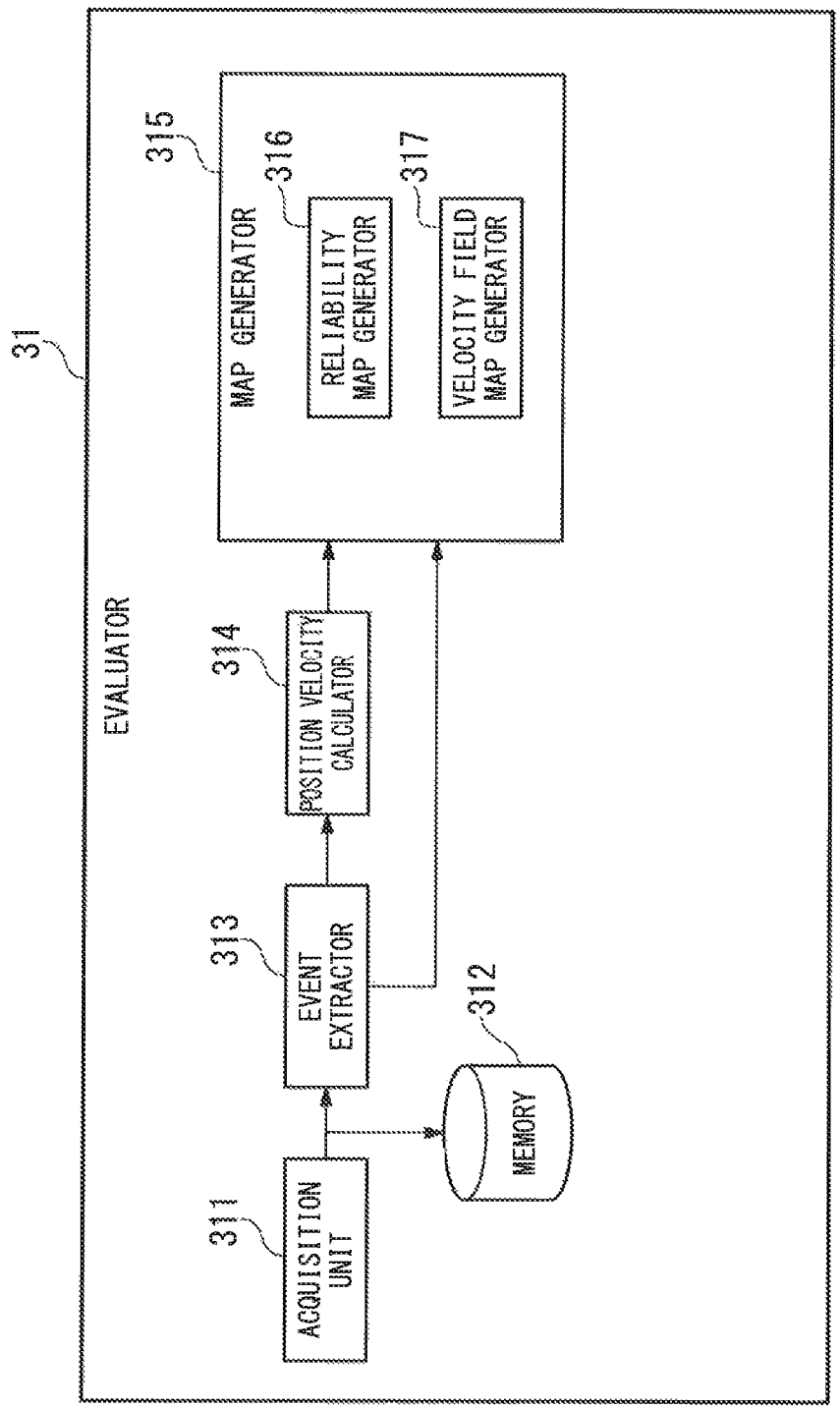
FIG. 3 is a schematic block diagram illustrating a function of an evaluator 31.

FIG. 3 is a schematic block diagram illustrating a function of the evaluator 31. As illustrated in FIG. 3, the evaluator 31 includes an acquisitor 311, a memory 312, an event extractor 313, a position velocity calculator 314, and a map generator 315.

The acquisitor 311 acquires the transmission data output from the signal processor 20. The acquisitor 311 stores the acquired transmission data in the memory 312.

The memory 312 is configured using a storage device such as a magnetic hard disk device or a semiconductor storage device. The memory 312 stores the transmission data acquired by the acquisitor 311.

The event extractor 313 extracts transmission data of one event from the transmission data stored in the memory 312. An event represents a certain elastic wave generation event that occurs in a structure. When an event occurs one time in the structure due to the occurrence of cracks or the like therein, elastic waves are detected by the plurality of AE sensors 10 at substantially the same time. That is, transmission data related to elastic waves detected at substantially the same time are stored in the memory 312. Therefore, the event extractor 313 provides a predetermined time window and extracts all transmission data whose arrival time is within the range of the time window as the transmission data of one event. The event extractor 313 outputs the extracted transmission data of one event to the position velocity calculator 314 and the map generator 315.

By using an elastic wave propagation velocity v in a target structure and the maximum sensor interval $d_{max}$, a range Tw of the time window may be determined to be in the range, $Tw \geq d_{max}/v$. To avoid erroneous detection, because it is preferable that Tw be set as small as possible, Tw may substantially be set as $Tw = d_{max}/v$.

Based on a plurality of pieces of transmission data extracted by the event extractor 313, the position velocity calculator 314 locates a position of a source of an elastic wave and an elastic wave propagation velocity in the structure. The Kalman filter, a least-squares method, or the like may be used for locating the position of the source of the elastic wave and the elastic wave propagation velocity in the structure. The position velocity calculator 314 outputs information on the located position of the source of the elastic wave and the elastic wave propagation velocity in the structure to the map generator 315.

The map generator 315 includes a reliability map generator 316 and a velocity field map generator 317. The reliability map generator 316 generates a reliability map indicating the soundness of the evaluation region on the basis of the reliability information included in the transmission data of one event output from the event extractor 313 and the position of the source of the elastic wave. The velocity field map generator 317 generates the reliability map generated by the reliability map generator 316 and a velocity field map indicating the relationship between the velocity and the reliability in the evaluation region of the structure.

Figure 4:
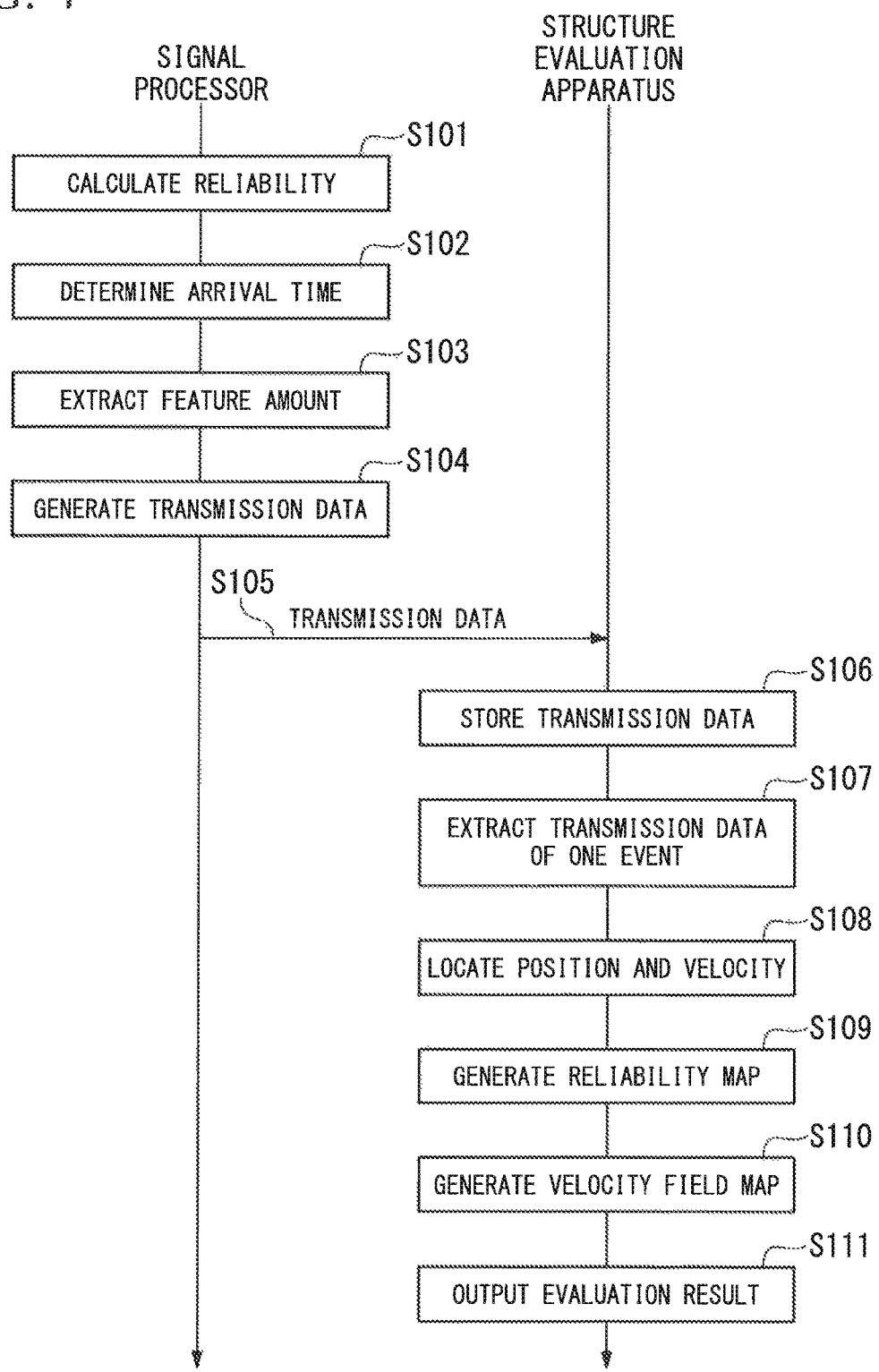
FIG. 4 is a sequence diagram illustrating a process flow of the structure evaluation system 100.

FIG. 4 is a sequence diagram illustrating a process flow of the structure evaluation system 100. Also, in the process of FIG. 4, only characteristic processing using the signal processor 20 and the structure evaluation apparatus 30 will be described.

Based on the input gate signal, the reliability calculator 203 calculates the reliability of the noise-removed AE signal while the waveform of the noise-removed AE signal is continued (Step S101). Here, the method of calculating the reliability will be described in detail. When data at a time t is $x_t$ and a probability model of a signal amplitude is $P_t$, the Shannon's information quantity Score $(x_t)$ is an index indicating the unexpectedness of the data $x_t$ at the current time t with respect to a past probability model $P_{t-1}$ based on past data up to time t−1, and is expressed by Equation 1 below.

[Math. 1]

$$\text{Score}(x_t) = -\log P_{t-1}(x_t) \quad (1)$$

Here, when for example, a normal distribution model is assumed as the probability model P, the probability density function at the time t is expressed by Equation 2 below.

[Math. 2]

$$P_t(x) = \frac{1}{\sqrt{2\pi\hat{\sigma}_t^2}} \exp\left\{-\frac{(x-\hat{\mu}_t)^2}{2\hat{\sigma}_t^2}\right\} \quad (2)$$

In Equation 2, $\hat{\mu}_t$ (^ on top of μ) represents an average, and $\hat{\sigma}_t^2$ (^ on top of σ) represents a variance-average. To smooth the Shannon's information quantity, an integer T is given and a T-average score series $y_t$ of a window width T expressed by Equation 3 below is obtained.

[Math. 3]

$$y_t = \frac{1}{T} \sum_{\tau=t-T+1}^{t} \text{Score}(x_i) \quad (3)$$

Also, when calculating the Shannon's information quantity again using the smoothened value, the reliability calculator 203 prepares a normal distribution model again for the time-series data $y_t$, obtains the probability density function $Q_t$, and calculates the Shannon's information quantity of $y_t$ with respect to a past model $Q_{t-1}$ based on past data as shown in Equation 4 below.

[Math. 4]

$$\text{Score}(y_t) = -\log Q_{t-1}(y_t) \quad (4)$$

Then, an integer T' is given to obtain a T'-average score of a window width T' expressed by Equation 5 below.

[Math. 5]

$$\text{Score}(t) = \frac{1}{T'} \sum_{i=t-T'+1}^{t} \text{Score}(y_i) \quad (5)$$

The reliability calculator 203 may calculate the Shannon's information amount expressed by Equation 1 above and use the calculated Shannon's information as the reliability, may calculate a value obtained by smoothing the Shannon's information quantity as shown in Equation 3 above and use the calculated value as the reliability, or may calculate a Shannon's information quantity again, calculate a value obtained by smoothing the re-calculated Shannon's information quantity, and use the calculated value as the reliability as shown in Equation 4 and Equation 5. When the structure is deteriorated, the reliability value is lower than when the structure is not deteriorated.

Next, the arrival time determiner 204 determines the arrival time on the basis of the noise-removed AE signal (Step S102). Based on the gate signal, the feature amount extractor 205 extracts the feature amount of the noise-removed AE signal when the waveform of the noise-removed AE signal is continued (Step S103). The transmission data generator 206 generates transmission data by associating the information acquired in the processing from Step S101 to Step S103 (Step S104). The output 208 outputs the generated transmission data to the structure evaluation apparatus 30 (Step S105). Further, the processing from Step S101 to Step S105 is executed each time an elastic wave is detected by the AE sensor 10. That is, the reliability, the arrival time, and the feature amount are acquired for each elastic wave detected by the AE sensor 10.

The acquisitor 311 acquires the transmission data output from the signal processor 20 and stores the acquired transmission data in the memory 312 (Step S106). The event extractor 313 extracts the transmission data of one event from the transmission data stored in the memory 312 (Step S107). Further, when the number of pieces of transmission data of one event is smaller than the number required for locating the position and the velocity (e.g., two), the event extractor 313 extracts a number of pieces of transmission data of one event which is larger than the number required for locating the position and the velocity.

Based on the extracted transmission data of one event, the position velocity calculator 314 locates the position of the source and the velocity of the elastic wave generated during one event (Step S108). Hereinafter, a method of deriving the position of the source and the velocity of the elastic wave will be described in detail. A three-dimensional coordinate system with one of the plurality of AE sensors 10 as the origin is considered. When the number of AE sensors 10 is n, an arrival time difference $\Delta t_i$ between an AE sensor $S_0$ at the origin and other AE sensors $S_i$ (i =1, 2,. . . , n−1) is shown as Equation 6 below, where coordinates of a source of an elastic wave are $(X_s, y_s, z_s)$, coordinates of an AE sensor Si are $(a_i, b_i, c_i)$, and an elastic wave propagation velocity is v.

[Math. 6]

$$\Delta t_i = \frac{\sqrt{(x-a_i)^2 + (y-b_i)^2 + (z-c_i)^2} - \sqrt{x^2 + y^2 + z^2}}{v} \quad (6)$$

The observed value is $\Delta t_i$, and nonlinear simultaneous equations with n−1 $(x_s, y_s, z_s, v)$ as unknowns is obtained for n sensors. The unknowns $(x_s, y_s, z_s, v)$ may be found by using various approximate solutions. Also, the position velocity calculator 314 calculates an average velocity of the elastic wave propagation velocity v. The reliability map generator 316 generates a reliability map on the basis of the located position of the source of the elastic wave and the reliability value included in the transmission data (Step S109). Also, the velocity field map generator 317 generates a velocity field map on the basis of the generated reliability map, the located position of the source of the elastic wave, the elastic wave propagation velocity v, and the average velocity (Step S110).

Figure 5A:
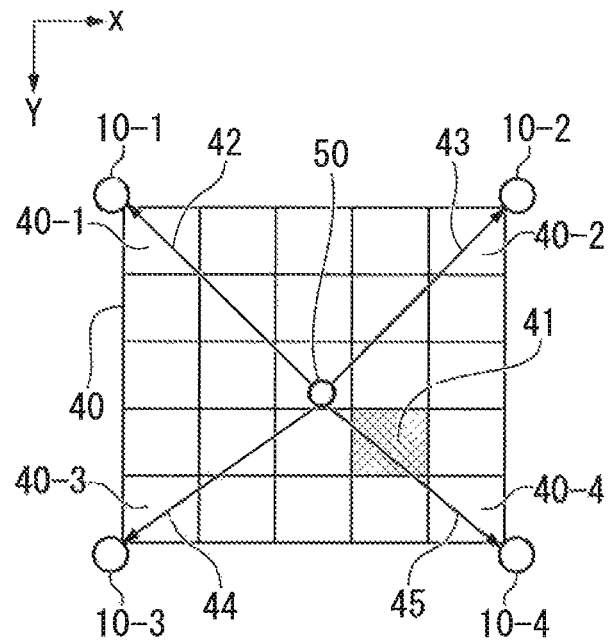
FIG. 5A is a view for describing a process for generating a reliability map and a velocity field map.
Figure 5B:
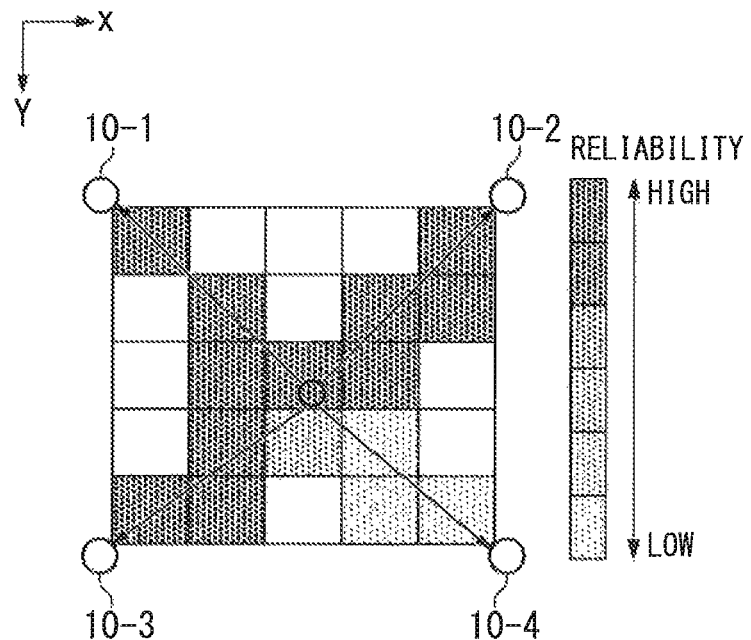
FIG. 5B is a view for describing a process for generating a reliability map and a velocity field map.
Figure 5C:
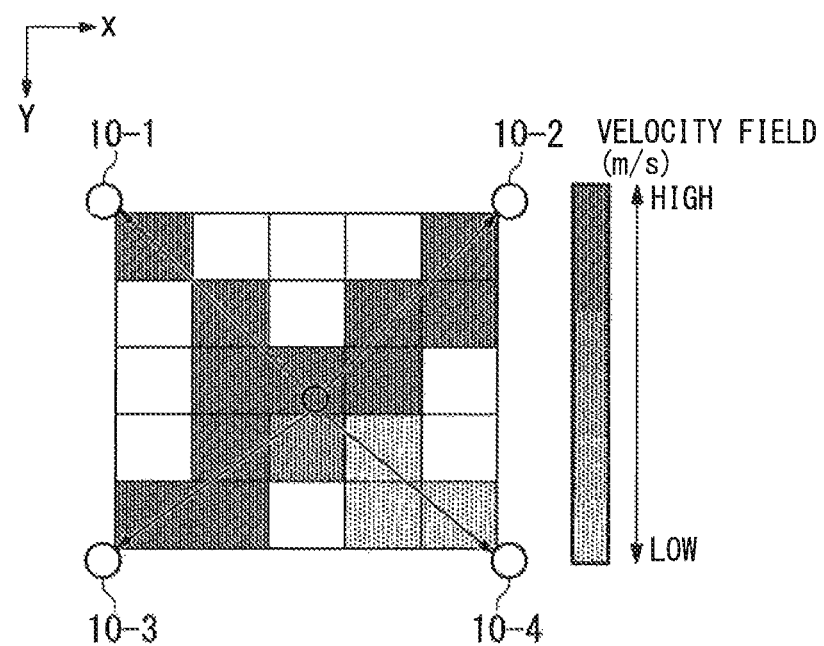
FIG. 5C is a view for describing a process for generating a reliability map and a velocity field map.

FIGS. 5A, 5B and SC are each a view for describing a process for generating a reliability map and a velocity field map. In the description of FIGS. 5A, 5B and 5C. AE sensors 10 (AE sensors 10-1 to 10-4) are assumed as being respectively installed at four corners of an evaluation region 40 to be evaluated for the soundness of the structure. Also, the map generator 315 is assumed as having sensor IDs and installation positions of the AE sensors 10 provided in the evaluation region 40 pre-stored therein. Also, the map generator 315 holds the reliability of each of the AE sensors 10 from the output from the event extractor 313 and holds the position of the source of the elastic wave, the elastic wave propagation velocity v, and the average velocity from the output from the position velocity calculator 314.

First, the process of generating the reliability map will be described. The reliability map generator 316 divides the evaluation region 40 into a plurality of regions. As a result, the evaluation region 40 is divided into a plurality of regions (for example, twenty-five regions) as illustrated in FIG. 5A. Hereinafter, each of the divided regions will be referred to as a divided region. Further, the interval at which the evaluation region is divided may be preset. Here, for simplicity of description, the divided regions shown in FIG. 5A are distinguished by combinations of x-coordinates and y-coordinates with the position where the AE sensor 10-1 is installed as a reference. Then, a divided region 40-1 is represented by (x, y)=(1, 1), a divided region 40-2 is represented by (x, y)=(5, 1), a divided region 40-3 is represented by (x, y)=(1, 5), and a divided region 40-4 is represented by (x, y)=(5, 5).

Next, on the basis of information on the installation positions of the AE sensors 10, a position of a source 50 of an elastic wave, and information on the range (e.g., coordinates) of each of the divided regions in the evaluation region, the reliability map generator 316 estimates a divided region through which the elastic wave has passed on a movement path of the elastic wave from the source 50 of the elastic wave to each of the AE sensors 10. For example, as illustrated in FIG. 5A, the reliability map generator 316 assumes that the movement path of the elastic wave from the source 50 of the elastic wave to each of the AE sensors 10 is a straight line and estimates divided regions through which the elastic wave has passed.

Specifically, the reliability map generator 316 estimates that divided regions through which an elastic wave 42 has passed on the movement path of the elastic wave from the source 50 of the elastic wave to the AE sensor 10-1 are four divided regions represented by coordinates (1, 1), (2, 2), (2, 3), (3, 3). Also, the reliability map generator 316 estimates that divided regions through which an elastic wave 43 has passed on the movement path of the elastic wave from the source 50 of the elastic wave to the AE sensor 10-2 are five divided regions represented by coordinates (5, 1), (5, 2), (4, 2), (4, 3), (3, 3). Also, the reliability map generator 316 estimates that divided regions through which an elastic wave 44 has passed on the movement path of the elastic wave from the source 50 of the elastic wave to the AE sensor 10-3 are four divided regions represented by coordinates (1, 5), (2, 4), (2, 5), (3, 4). Also, the reliability map generator 316 estimates that divided regions through which an elastic wave 45 has passed on the movement path of the elastic wave from the source 50 of the elastic wave to the AE sensor 10-4 are four divided regions represented by coordinates (3, 4), (4, 4), (4, 5), (5, 5).

The reliability map generator 316 generates a reliability map by assigning a value corresponding to the reliability to the estimated divided region. Specifically, the reliability map generator 316 assigns a value corresponding to the reliability obtained from the elastic wave detected by the AE sensor 10-1, to the four divided regions through which the elastic wave 42 has passed on the movement path of the elastic wave from the source 50 of the elastic wave to the AE sensor 10-1. For example, the reliability map generator 316 may assign a reliability value as a value of a divided region or assign a value obtained by performing predetermined processing on a reliability value as a value of a divided region. The reliability map generator 316 performs the same processing for other divided regions through which the elastic waves have passed.

Here, when deterioration has occurred in a divided region 41 (coordinates (x, y)=(4, 4)) in FIG. 5A, the reliability obtained from the elastic wave detected by the AE sensor 10-4 is lower than the reliability obtained from the elastic waves detected by other AE sensors 10. This is because when the elastic wave passes through the region where deterioration is occurring, the velocity decreases and the signal-to-noise ratio (S/N) decreases. Likewise, in such a case, the map generator 315 assigns a value corresponding to the reliability obtained from the elastic wave detected by the AE sensor 10-4 to the four divided regions through which the elastic wave 45 has passed.

Also, when a plurality of elastic waves pass through the same divided region, as for a divided region represented by coordinates (3, 4) in FIG. 5A, the map generator 315 determines a value to be assigned to a single divided region through which a plurality of elastic waves pass using a few methods described below. As a first method, the map generator 315 calculates an average value of a plurality of reliability values obtained from elastic waves detected by AE sensors 10 (In FIG. 5A, the AE sensors 10-3 and 10-4) that have detected elastic waves passing through a single divided region (in FIG. 5A, the divided region represented by coordinates (3, 4)) through which a plurality of elastic waves pass, and determines the calculated average value as a value to be assigned to the single divided region through which the plurality of elastic waves pass. As a second method, the map generator 315 determines a value obtained according to a length of a distance each elastic wave has passed within a single divided region through which a plurality of elastic waves pass as a value to be assigned to the single divided region through which the plurality of elastic waves pass. For example, when two elastic waves pass through a single divided region, the map generator 315 assigns a larger weight to a reliability obtained from an elastic wave that has passed over a longer distance through a divided region than to a reliability obtained from an elastic wave that has passed over a shorter distance through the divided region, and determines a value obtained by summing the obtained values as a value to be assigned to the single divided region through which the plurality of elastic waves pass.

FIG. 5B illustrates a reliability map generated as described above. As illustrated in FIG. 5B, it can be seen that the reliability is low, i.e., deterioration is occurring, near where the AE sensor 10-4 is installed.

Next, the process of generating a velocity field distribution will be described. Like the process by the reliability map generator 316, the velocity field map generator 317 generates a velocity field map by assigning a value, obtained by assigning weights to elastic wave propagation velocities v of elastic waves located by the position velocity calculator 314 according to reliability, to a divided region through which an elastic wave has passed. Here, the elastic wave propagation velocity v and the reliability are decreased when an elastic wave passes through a damaged region of a structure. Consequently, when assigning weights according to reliability, the velocity field map generator 317, for example, assigns weights so that the velocity is higher when the reliability is higher and the velocity is lower when the reliability is lower. An average velocity is a standard for determining whether the elastic wave propagation velocity v is high or small. That is, the velocity field map generator 317 assigns a velocity higher than the average velocity to a divided region when the reliability thereof is higher, and assigns a velocity lower than the average velocity to a divided region when the reliability thereof is lower.

FIG. 5C illustrates a velocity field map generated as described above. As illustrated in FIG. 5C, as in FIG. 5B, it can be seen that the elastic wave propagation velocity v is low, i.e., deterioration is occurring, near where the AE sensor 10-4 is installed. Then, the reliability map generator 316 and the velocity field map generator 317 output evaluation results to the output 32. The output 32 outputs the evaluation results (Step S Ill). For example, the output 32 displays the reliability map as a contour map corresponding to high and low levels of reliability. Further, the output 32 displays the velocity field map as a contour map corresponding to the high and low levels of the velocity field.

Figure 6A:
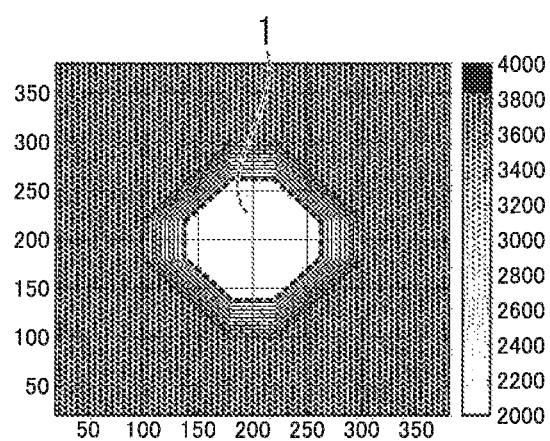
FIG. 6A is a view illustrating simulation results for a structure evaluation apparatus 30.
Figure 6B:
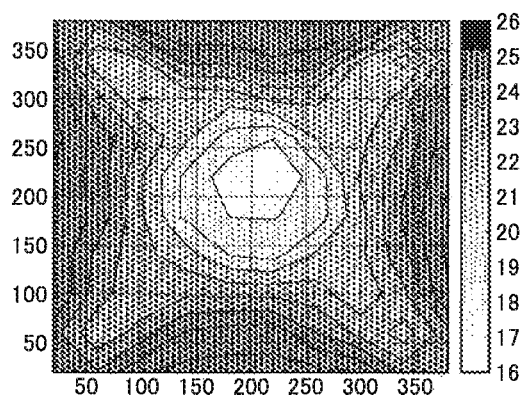
FIG. 6B is a view illustrating simulation results for a structure evaluation apparatus 30.
Figure 6C:
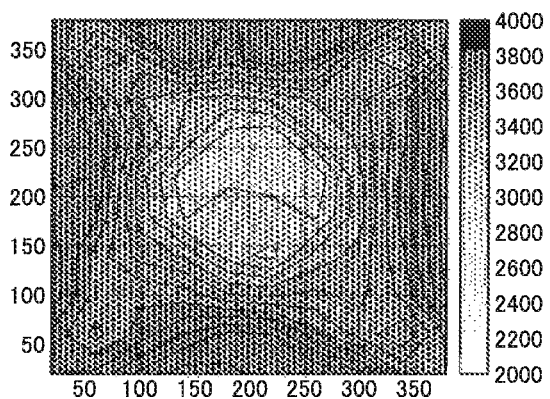
FIG. 6C is a view illustrating simulation results for a structure evaluation apparatus 30.
Figure 6D:
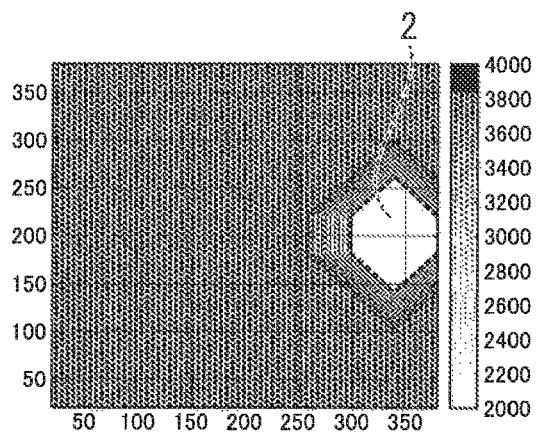
FIG. 6D is a view illustrating simulation results for a structure evaluation apparatus 30.
Figure 6E:
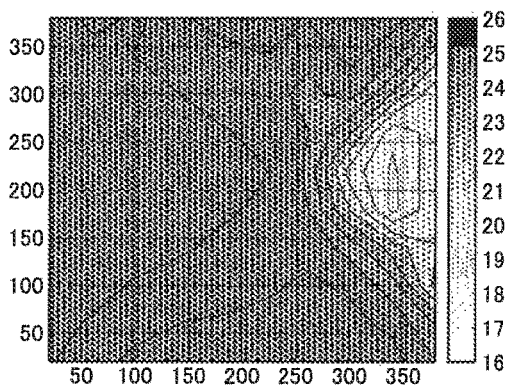
FIG. 6E is a view illustrating simulation results for a structure evaluation apparatus 30.
Figure 6F:
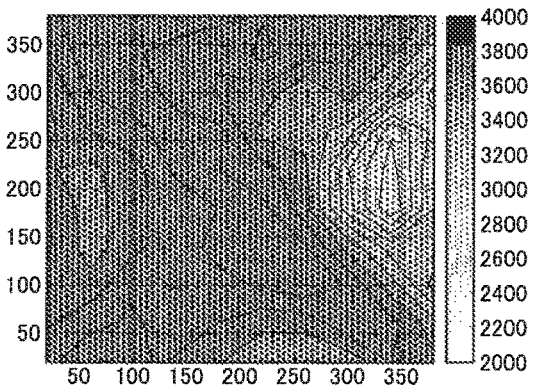
FIG. 6F is a view illustrating simulation results for a structure evaluation apparatus 30.

FIGS. 6A, 6B, 6C, 6D, 6E and 6F are each a view illustrating simulation results for the structure evaluation apparatus 30. In each drawing of FIGS. 6A, 6B, 6C, 6D, 6E and 6F, the vertical axis and the horizontal axis represent the size of an evaluation region. In FIGS. 6A and 6D represent two structure models prepared for simulation. Region 1 indicated by a broken line in FIG. 6A and Region 2 indicated by a broken line in FIG. 6D represent a region assumed to be damaged (a damaged region). In contrast, a dense shaded region of the structure model represents a sound region. FIG. 6B represents a reliability map of the result of simulation using the structure model of FIG. 6A, and FIG. 6C shows a velocity field map of the result of simulation using the structure model of FIG. 6A. Also, FIG. 6E represents a reliability map of the result of simulation using the structure model of FIG. 6D, and FIG. 6F shows a velocity field map of the result of simulation using the structure model of FIG. 6D.

The simulation results shown in FIGS. 6B, 6C, 6E and 6F are results of analyzing based on the method proposed herein, by placing the AE sensors 10 at each of the four corners of a square with each side being 400 mm and randomly generating elastic waves a hundred times within the 400 mm×400 mm region surrounded by the AE sensors 10 in the two structure models. The elastic wave velocities in a sound region and a damaged region are 4000 m/s and 2000 m/s, respectively. From the simulation results shown in FIGS. 6B, 6C, 6E and 6F, it can be seen that regions corresponding to damaged regions shown in the structure models FIGS. 6A and 6B are results reflecting the damaged regions in the reliability maps and the velocity field maps.

According to the structure evaluation system 100 configured as described above, the time required for evaluating a structure can be reduced. Specifically, the structure evaluation system 100 acquires a reliability from an elastic wave and generates a reliability map using the acquired reliability. As a result, because a process of iterative calculation by the conventional simultaneous iterative method can be omitted, the calculation time is reduced significantly. Therefore, the time required for evaluating a structure can be reduced.

Furthermore, by generating a reliability map of a structure as well as a velocity field map thereof, information of the structure that cannot be detected using only a velocity field can be detected.

Hereinafter, a modified example of the structure evaluation system 100 will be described.

The AE sensor 10 may incorporate the amplifier 11. In this case, the structure evaluation system 100 may not include the amplifier 11.

Although the evaluator 31 is described in the above embodiment as evaluating a structure by generating a reliability map and a velocity field map, the evaluator 31 may evaluate a structure by generating only the reliability map.

When a reliability map is newly generated, the evaluator 31 may be configured to update a reliability map using reliability maps of the same evaluation region generated up to a previous time and the newly generated reliability map. The reliability map, created prior to the last time, for the same evaluation region refers to a reliability map, created prior to creating a last-created reliability map, for the same evaluation region. In this case, for example, the evaluator 31 calculates, for each of the divided regions, an average value of reliability values in the divided regions of the reliability maps generated so far including the newly generated reliability map, and updates the reliability map by assigning the calculated values to each of the divided regions as an updated value. Also, like the reliability map, for a velocity field map, the evaluator 31 updates a velocity field map using a velocity field map obtained from a newly generated reliability map and velocity field maps generated up to a previous time. In this case, for example, the evaluator 31 calculates, for each of the divided regions, an average value of elastic wave propagation velocities v in the divided regions of the velocity field maps generated so far including the newly generated reliability map, and updates the velocity field map by assigning the calculated values to each of the divided regions as an updated value. The velocity field map, created prior to the last time, for the same evaluation region refers to a velocity field map, created prior to creating a last-created velocity field map, for the same evaluation region.

This is shown in detail in FIGS. 7A to 7D.

Figure 7A:
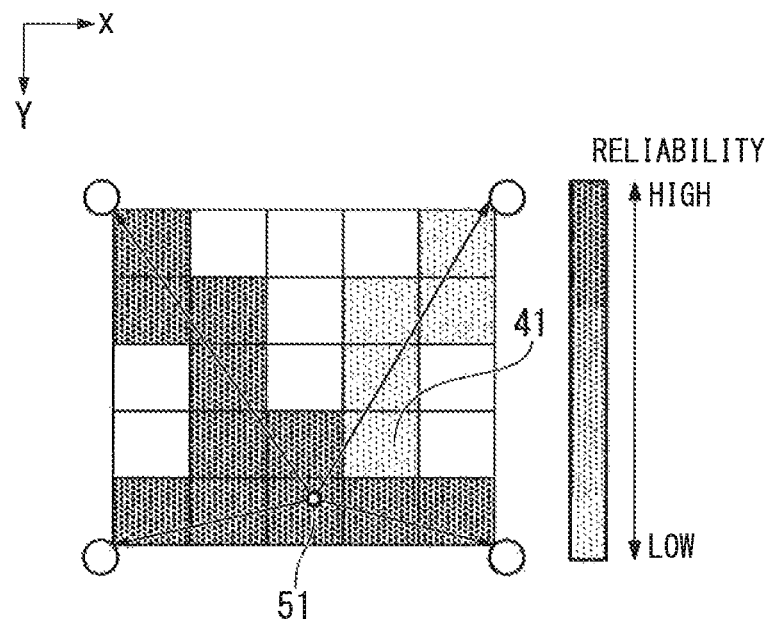
FIG. 7A is a view for describing a process for updating a reliability map and a velocity field map.
Figure 7B:
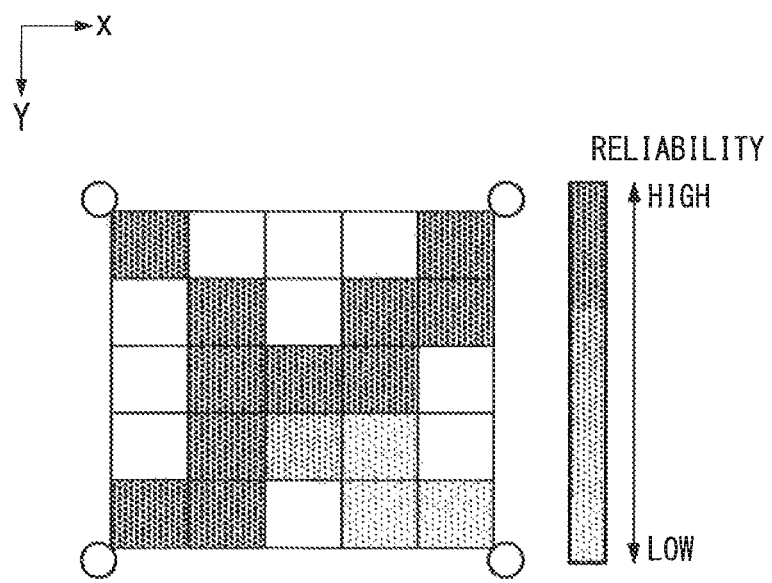
FIG. 7B is a view for describing a process for updating a reliability map and a velocity field map.

FIG. 7A shows a newly generated reliability map, and FIG. 7B shows a reliability map generated up to a previous time. In FIG. 7B, for example, the reliability map shown in FIG. 5B is used as the reliability map generated up to the previous time, assuming that the reliability map has been generated only once up to the previous time. In FIG. 7A, a source 51 of an elastic wave is present in a region different from the region shown in FIG. 5A. In FIG. 7A, because the reliability map is generated for the same evaluation region as in FIG. 5A, deterioration is occurring in the divided region 41.

Figure 7C:
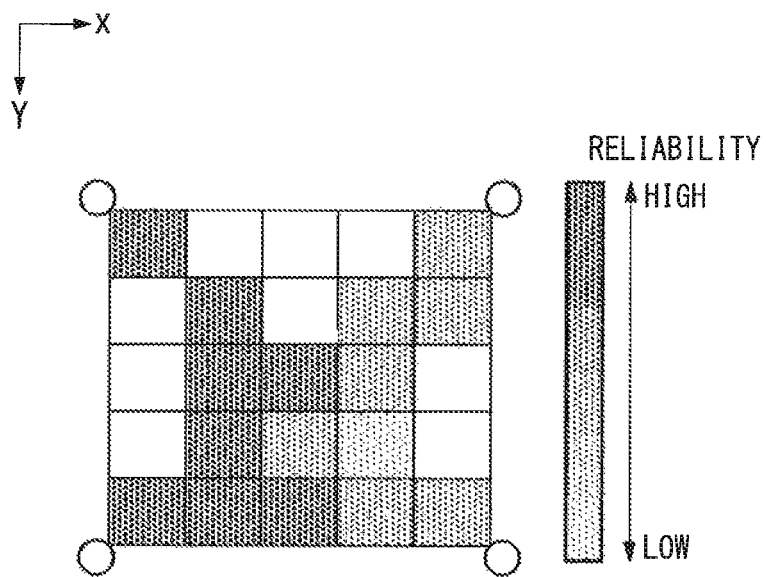
FIG. 7C is a view for describing a process for updating a reliability map and a velocity field map.
Figure 7D:
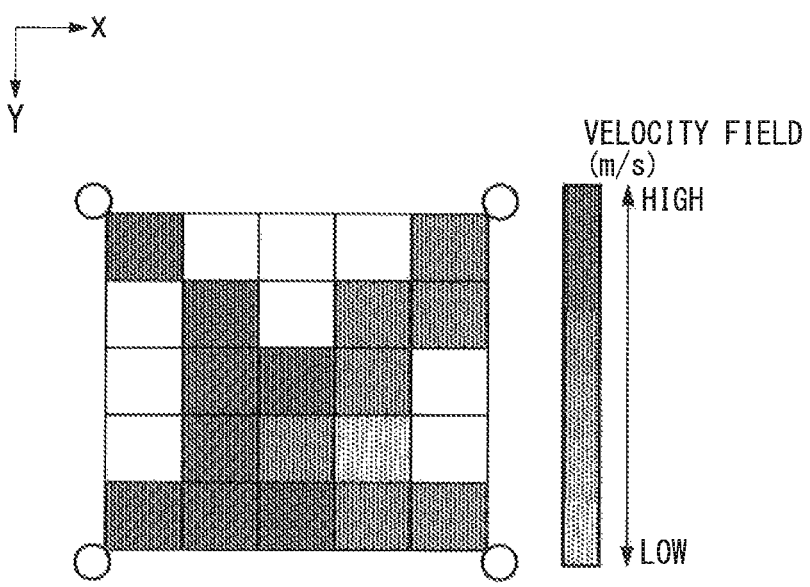
FIG. 7D is a view for describing a process for updating a reliability map and a velocity field map.

Using the reliability map shown in FIG. 7A and the reliability map shown in FIG. 7B, the reliability map generator 316 calculates, for each of the divided regions, the average value of the values assigned to the divided regions. Then, the reliability map generator 316 updates the reliability map by assigning the calculated values to each of the divided regions as an update value. The updated reliability map is shown in FIG. 7C. Also, the updated velocity field map is shown in FIG. 7D.

With the above configuration, when the reliability map and the velocity field map are updated, the reliability and the elastic wave propagation velocity v of the region where deterioration is occurring are lower than those in other regions. Therefore, by updating the reliability map and the velocity field map, a region where deterioration is occurring can be accurately detected.

Although the map generator 315 is described in the above embodiment as using all reliability maps and velocity field maps generated in the past when updating a reliability map and a velocity field map, embodiments are not necessarily limited thereto. For example, when updating a reliability map and a velocity field map, the map generator 315 may be configured to use a reliability map and a velocity field map generated up to several times in the past several times (e.g., once in the past, twice in the past, etc.)

(Second Embodiment)

Figure 8:
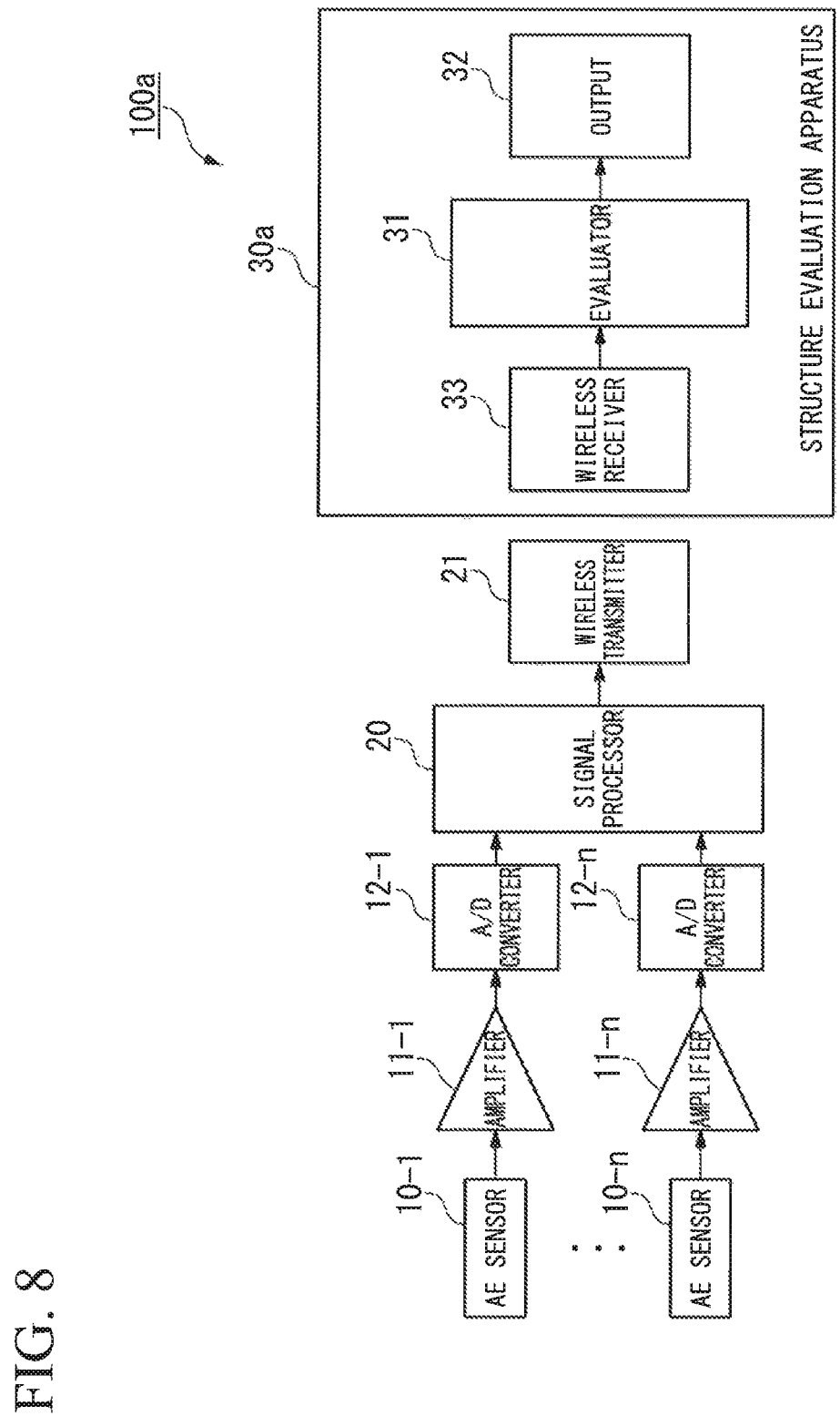
FIG. 8 is a view illustrating a system configuration of a structure evaluation system 100a according to a second embodiment.

FIG. 8 is a view illustrating a system configuration of a structure evaluation system 100a according to a second embodiment. The structure evaluation system 100a includes the plurality of AE sensors 10-1 to 10-n, the plurality of amplifiers 11-1 to 11-n, the plurality of A/D converters 12-1 to 12-n, the signal processor 20, a wireless transmitter 21, and a structure evaluation apparatus 30a, the structure evaluation apparatus 30a includes the evaluator 31, the output 32, and a wireless receiver 33, in the second embodiment, the signal processor 20 and the structure evaluation apparatus 30a are connected by wireless communication, in this case, the wireless transmitter 21 transmits transmission data output from the signal processor 20 to the structure evaluation apparatus 30a. The wireless receiver 33 receives the transmission data transmitted from the wireless transmitter 21 and outputs the received transmission data to the evaluator 31. A so-called industry science medical (ISM) band including, for example, 2.4 GHz and 920 MHz band (915 MHz to 928 MHz in Japan) can be used as the wireless frequency band between the wireless transmitter 21 and the wireless receiver 33.

With the above configuration, the AE sensor 10, the amplifier 11, the A/D converter 12, the signal processor 20, and the wireless transmitter 21 can be set as sensor nodes and installed in a structure such as a bridge to be evaluated, the structure evaluation apparatus 30a can be installed in a monitoring room, and a deteriorated state of the structure may be monitored from a remote place.

Like the first embodiment, the second embodiment may also be modified.

(Third Embodiment)

Figure 9:
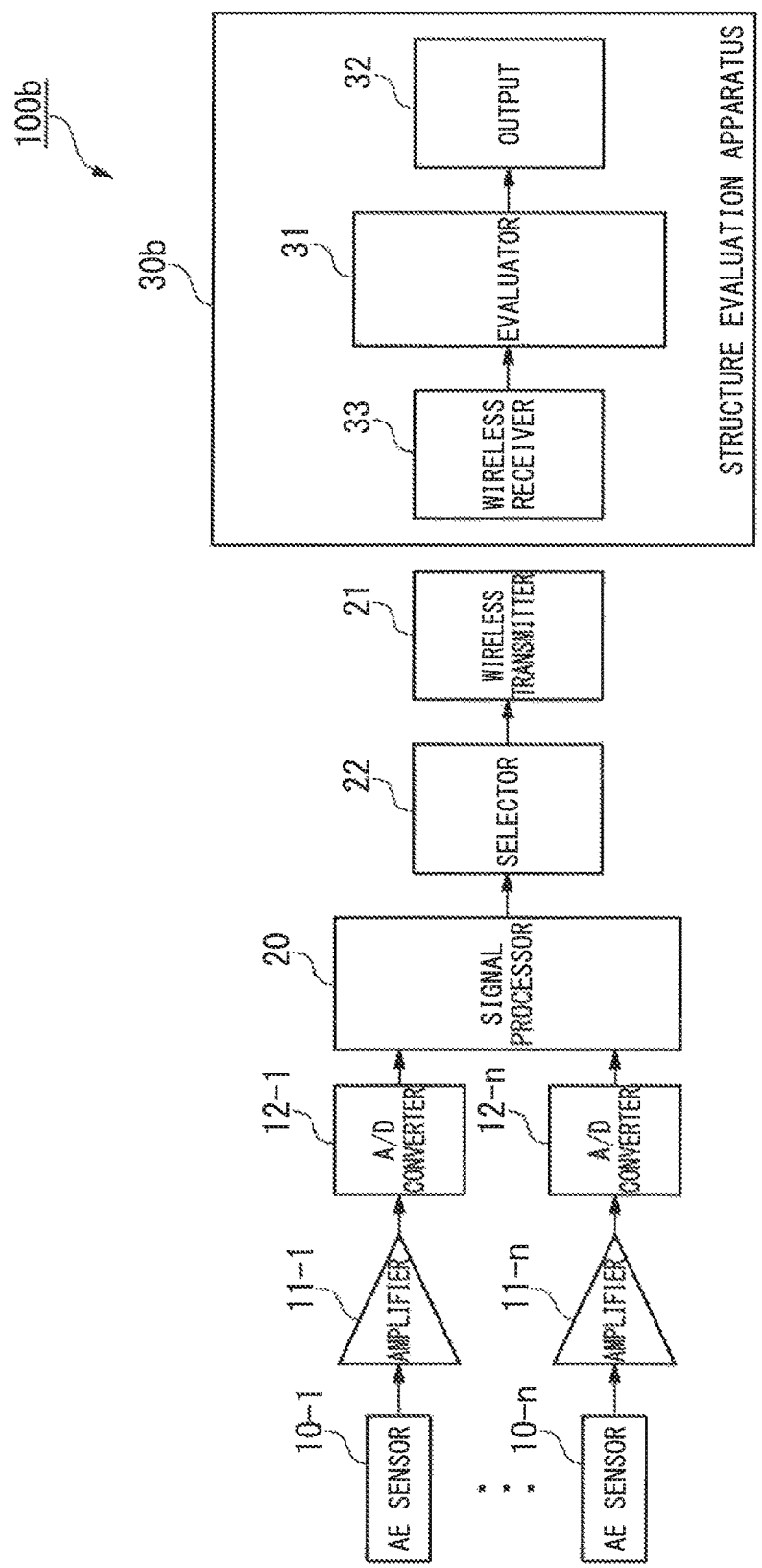
FIG. 9 is a view illustrating a system configuration of a structure evaluation system 100b according to a third embodiment.

FIG. 9 is a view illustrating a system configuration of a structure evaluation system 100b according to a third embodiment. The structure evaluation system 100b includes the plurality of AE sensors 10-1 to 10-n, the plurality of amplifiers 11-1 to 11-n, the plurality of A/D converters 12-1 to 12-n, the signal processor 20, the wireless transmitter 21, a selector 22, and a structure evaluation apparatus 30b. The structure evaluation apparatus 30b includes the evaluator 31, the output 32, and the wireless receiver 33. The selector 22 selects transmission data to be used for evaluation according to information of reliability and a feature amount of a signal. For example, the selector 22 may output only the transmission data in which an amplitude in a feature amount of a signal is a predetermined threshold value or larger to the wireless transmitter 21. Also, the selector 22 may output only the transmission data in which the reliability of a signal is a predetermined threshold value or higher to the wireless transmitter 21.

With the above configuration, transmitting unnecessary noise information as transmission data is suppressed, and power consumption on a transmission side can be reduced. Also, deterioration of structure evaluation caused by transmitting unnecessary noise information as transmission data can be suppressed.

In the structure evaluation system 100b, the wireless transmitter 21 and the wireless receiver 33 may not be provided. In this case, the selector 22 outputs the transmission data selected as described above to the structure evaluation apparatus 30b.

Like the first embodiment, the third embodiment may also be modified.

According to at least one embodiment described above, the time required for structure evaluation can be reduced by having the plurality of AE sensors 10 configured to detect elastic waves generated from a structure, the signal processor 20 configured to acquire a reliability by performing signal processing on elastic waves, and the evaluator 31 configured to evaluate the soundness of the structure on the basis of the acquired reliability.

In each of the embodiments described above, the signal processor 20 may be provided in the structure evaluation apparatus 30. In this case, in the second embodiment, the signal processor 20 and the wireless transmitter 21 are provided in the structure evaluation apparatus 30a. Also, in the third embodiment, the signal processor 20, the wireless transmitter 21, and the selector 22 are provided in the structure evaluation apparatus 30b.

The following supplementary notes will be disclosed regarding the structure evaluation system 100 shown in the embodiments.

(Supplementary Note 1)

A structure evaluation system including:

a plurality of sensors configured to detect an elastic wave generated from a structure;

a signal processor configured to acquire a reliability of an elastic wave from a source of the elastic wave to the plurality of sensors by performing signal processing on the elastic wave detected by the plurality of sensors; and an evaluator configured to locate a velocity of the elastic wave on the basis of an arrival time of the elastic wave and evaluate soundness of the structure on the basis of the velocity and the acquired reliability.

(Supplementary Note 2)

The structure evaluation system according to supplementary note 1, wherein, on the basis of the velocity and the acquired reliability, the evaluator generates a velocity field map indicating a relationship between the velocity and the reliability in an evaluation region of the structure.

(Supplementary Note 3)

The structure evaluation system according to supplementary note 2, wherein the evaluator generates the velocity field map so that the velocity is higher for a region with a higher reliability on the velocity field map and is lower for a region with a lower reliability on the velocity field map.

(Supplementary Note 4)

The structure evaluation system according to any one of supplementary notes 1 to 3, wherein, when a velocity field map is newly generated, the evaluator updates a velocity field map using velocity field maps of the same evaluation region generated up to the previous time and the newly generated velocity field map.

Although a few embodiments of the present invention have been described above, the embodiments are merely examples and are not intended to limit the scope of the invention. The embodiments may be implemented in various other forms, and various omissions, substitutions, and changes can be made to the embodiments within the scope not departing from the gist of the invention. The embodiments and modifications thereof belong to the claims below and their equivalents as well as the scope and gist of the invention.

REFERENCE SIGNS LIST 10 (10-1 to 10-*n*) AE sensor
11 (11-1 to 11-*n*) Amplifier
12 (12-1 to 12-*n*) A/D converter
20 Signal processor
30 Structure evaluation apparatus
31 Evaluator
32 Output
201 Waveform shaping filter
202 Gate generation circuit
203 Reliability calculator
204 Arrival time determiner
205 Feature amount extractor
206 Transmission data generator
207 Memory
208 Output
311 Acquisitor
312 Memory
313 Event extractor
314 Position velocity calculator
315 Map generator
316 Reliability map generator
317 Velocity field map generator

The invention claimed is:

1. A structure evaluation system comprising:
a plurality of sensors configured to detect an elastic wave generated from a structure;
a signal processor configured to acquire a reliability of the elastic wave on the basis of the elastic wave detected by the plurality of sensors; and
an evaluator configured to evaluate soundness of the structure on the basis of the acquired reliability,
wherein the signal processor comprises a waveform shaping filter or a gate generation circuit,
wherein the reliability is a value indicating a degree of unexpectedness of the latest data with respect to past statistical data,
wherein the signal processor divides an evaluation region of the structure to be evaluated for soundness into a plurality of regions and acquires the reliability of the elastic wave in a region through which the elastic wave passes on a movement path of the elastic wave from a source of the elastic wave to the plurality of sensors among the plurality of regions.

2. The structure evaluation system according to claim 1, wherein the evaluator divides an evaluation region of the structure to be evaluated for soundness into a plurality of regions and assigns a numerical value according to the reliability to each of the divided regions to generate a reliability map indicating soundness of the evaluation region.

3. The structure evaluation system according to claim 2, wherein, when a first reliability map is newly created, the evaluator updates a second reliability map using the second reliability maps of the same evaluation region created prior to creating the first reliability map.

4. The structure evaluation system according to claim 1, wherein the evaluator locates a velocity of the elastic wave on the basis of an arrival time of the elastic wave and generates a velocity field map indicating a relationship between the velocity and the reliability in the evaluation region of the structure using the velocity and the reliability map.

5. The structure evaluation system according to claim 4, wherein the evaluator generates the velocity field map so that the velocity is higher on the velocity field map with as a reliability is higher on the reliability map and is lower on the velocity field map with a reliability is lower on the reliability map.

6. The structure evaluation system according to claim 1, further comprising a selector configured to select data of an elastic wave to be used in the evaluation according to the reliability,
wherein the evaluator uses data and evaluates the soundness of the structure.

7. A structure evaluation apparatus comprising:
a signal processor configured to acquire a reliability of an elastic wave on the basis of the elastic wave generated from a structure; and
an evaluator configured to evaluate soundness of the structure on the basis of the acquired reliability,
wherein the signal processor comprises a waveform shaping filter or a gate generation circuit,
wherein the reliability is a value indicating a degree of unexpectedness of the latest data with respect to past statistical data,
wherein the signal processor divides an evaluation region of the structure to be evaluated for soundness into a plurality of regions and acquires the reliability of the elastic wave in a region through which the elastic wave passes on a movement path of the elastic wave from a source of the elastic wave to the plurality of sensors among the plurality of regions.

8. A structure evaluation method comprising:
a signal processing step of deriving a reliability of the elastic wave on the basis of the elastic wave detected by the plurality of sensor and
an evaluating step of deriving soundness of the structure on the basis of the reliability acquired,
the signal processing step is performed using a waveform shaping filter or a gate generation circuit, wherein the reliability is a value indicating a degree of unexpectedness of the latest data with respect to past statistical data, wherein the signal processing step includes dividing an evaluation region of the structure to be evaluated for soundness into a plurality of regions and acquiring the reliability of the elastic wave in a region through which the elastic wave passes on a movement path of the elastic wave from a source of the elastic wave to the plurality of sensors among the plurality of regions.

9. The structure evaluation system of claim 1, wherein the signal processor comprises a waveform shaping filter.

10. The structure evaluation system of claim 1, wherein the signal processor comprises a gate generation circuit.

11. The structure evaluation system of claim 1, wherein the signal processor comprises a waveform shaping filter and a gate generation circuit.

12. The structure evaluation apparatus of claim 7, wherein the signal processor comprises a waveform shaping filter.

13. The structure evaluation apparatus of claim 7, wherein the signal processor comprises a gate generation circuit.

14. The structure evaluation apparatus of claim 7, wherein the signal processor comprises a waveform shaping filter and a gate generation circuit.

15. The structure evaluation system of claim 8, wherein the signal processor comprises a waveform shaping filter.

16. The structure evaluation system of claim 8, wherein the signal processor comprises a gate generation circuit.

17. The structure evaluation system of claim 8, wherein the signal processor comprises a waveform shaping filter and a gate generation circuit.

* * * * *